US00PP20320P2

(12) United States Plant Patent
Oudshoorn

(10) Patent No.: US PP20,320 P2
(45) Date of Patent: Sep. 15, 2009

(54) *EUPATORIUM* PLANT NAMED 'BABY JOE'

(50) Latin Name: *Eupatorium purpureum*
Varietal Denomination: Baby Joe

(75) Inventor: Hubertus Gerardus Oudshoorn, Rijpwetering (NL)

(73) Assignee: Future Plants LIcentie B.V., Lisserbroek (NL)

( * ) Notice: Subject to any disclaimer, the term of this patent is extended or adjusted under 35 U.S.C. 154(b) by 0 days.

(21) Appl. No.: 12/214,238

(22) Filed: Jun. 16, 2008

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Eupatorium* plant named 'Baby Joe', characterized by its upright and relatively compact plant habit; moderately vigorous growth habit; freely flowering habit; large greyed purple-colored inflorescences; and strong and upright peduncles.

2 Drawing Sheets

Botanical designation: *Eupatorium purpureum.*
Cultivar denomination: 'Baby Joe'.

BACKGROUND OF THE INVENTION

The present invention relates to a new and distinct cultivar of *Eupatorium* plant, botanically known as *Eupatorium purpureum,* and hereinafter referred to by the name 'Baby Joe'.

The new *Eupatorium* is a product of a planned breeding program conducted by the Inventor in Rijpwetering, The Netherlands. The objective of the breeding program was to create new strong and compact Veronica cultivars with healthy foliage and attractive flower coloration.

The new *Eupatorium* originated from a cross-pollination of two unnamed selections of *Eupatorium purpureum,* not patented, as the female, or seed, parent with an unknown selection of *Eupatorium purpureum,* as the male, or pollen, parent. The new *Eupatorium* was discovered and selected by the Inventor as a single flowering plant from within the progeny of the stated cross-pollination grown in a controlled greenhouse environment in Rijpwetering, The Netherlands in September, 2003.

Asexual reproduction of the new *Eupatorium* by cuttings in a controlled greenhouse environment in Rijpwetering, The Netherlands since June, 2004, has shown that the unique features of this new *Eupatorium* are stable and reproduced true to type in successive generations.

SUMMARY OF THE INVENTION

Plants of the new *Eupatorium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Baby Joe'. These characteristics in combination distinguish 'Baby Joe' as a new and distinct cultivar of *Eupatorium:*

1. Upright and relatively compact plant habit.

2. Moderately vigorous growth habit.
3. Freely flowering habit.
4. Large greyed purple-colored inflorescences.
5. Strong and upright peduncles.

Compared to plants of the female parent selection, plants of the new *Eupatorium* are more compact. Compared to plants of the male parent selection, plants of the new *Eupatorium* are more freely flowering.

Plants of the new *Eupatorium* can be compared to plants of *Eupatorium maculatum* 'Atropurpureum', not patented. In side-by-side comparisons conducted in Rijpwetering, The Netherlands, plants of the new *Eupatorium* differed from plants of 'Atropurpureum' primarily in growth habit as plants of the new *Eupatorium* were more compact than plants of 'Atropurpureum'.

BRIEF DESCRIPTION OF THE PHOTOGRAPHS

The accompanying photographs illustrate the overall appearance of the new *Eupatorium.* The photographs show the colors as true as it is reasonably possible to obtain in colored reproductions of this type. Colors in the photographs may differ slightly from the color values cited in the detailed botanical description which accurately describe the colors of the new *Eupatorium.*

The photograph on the first sheet comprises a side perspective view of a typical flowering plant of 'Baby Joe' grown in a container.

The photograph at the top of the second sheet is a close-up view of typical inflorescences of 'Baby Joe'.

The photograph at the bottom of the second sheet is a close-up view of a typical leaf of 'Baby Joe'.

DETAILED BOTANICAL DESCRIPTION

The aforementioned photographs and following observations and measurements describe plants grown in Rijpwetering, The Netherlands during the summer in an outdoor nursery and under conditions and practices which approximate those generally used in commercial *Eupatorium* production. During the production of the plants, day temperatures ranged from 14° C. to 32° C. and night temperatures ranged from 4° C. to 15° C. Plants were six months from planting when the photographs and description were taken. In the following description, color references are made to The Royal Horticultural Society Colour Chart, 2001 Edition, except where general terms of ordinary dictionary significance are used.

Botanical classification: *Eupatorium purpureum* cultivar Baby Joe.

Parentage:

*Female parent.*—Unnamed selection of *Eupatorium purpureum,* not patented.

*Male parent.*—Unknown selection of *Eupatorium purpureum,* not patented.

Propagation:

*Type.*—By cuttings.

*Time to initiate roots.*—About one month at 17° C. to 27° C.

*Time to produce a rooted young plant.*—About six months at 15° C. to 28° C.

*Root description.*—Medium in thickness, fibrous; color, close to 161D.

*Rooting habit.*—Freely branching; dense.

Plant description:

*Plant form/growth habit.*—Herbaceous perennial. Relatively compact and upright plant habit; narrow inverted triangle; inflorescences held on strong and upright peduncles. Moderately vigorous growth habit.

*Plant height.*—About 44.7 cm.

*Plant diameter or spread.*—About 16.9 cm.

*Lateral branches.*—Length: About 32.5 cm. Diameter: About 5 mm. Internode length: About 3.5 cm. Aspect: Mostly upright. Strength: Strong. Texture: Smooth, glabrous. Color: Close to N186C.

Foliage description:

*Arrangement.*—Alternate, simple; sessile.

*Length.*—About 8.7 cm.

*Width.*—About 3.6 cm.

*Shape.*—Ovate.

*Apex.*—Acute to narrowly acuminate.

*Base.*—Attenuate.

*Margin.*—Serrate.

*Texture, upper surface.*—Smooth, glabrous.

*Texture, lower surface.*—Pubescent.

*Venation pattern.*—Pinnate.

*Color.*—Developing foliage, upper surface: Close to 141A. Developing foliage, lower surface: Close to 137C. Fully expanded foliage, upper surface: Close to 137B; venation, close to N186C. Fully expanded foliage, lower surface: Close to 146B; venation, close to 187A to 187B.

*Petioles.*—Length: About 1 cm. Diameter: About 2 mm by 3 mm. Color, upper surface: Close to N186C. Color, lower surface: Close to 187A.

Inflorescence description:

*Appearance.*—Discoid inflorescences arranged in compound corymbs. Inflorescences face mostly upright. Freely flowering habit; about 400 inflorescences develop per plant.

*Fragrance.*—Faint; sweet.

*Time to flower.*—Plants flower continuously during August and September in The Netherlands.

*Post-production longevity.*—Inflorescences maintain good substance for about three weeks on the plant. Inflorescences persistent.

*Inflorescence bud.*—Height: About 8 mm. Diameter: About 2.5 cm. Shape: Oblong. Color: Close to 186C; towards the base, close to 186B.

*Corymb diameter.*—About 12.9 cm.

*Corymb height.*—About 7.8 cm.

*Inflorescence diameter.*—About 1.7 cm.

*Inflorescence height.*—About 1.5 cm.

*Receptacle diameter.*—About 9 mm.

*Receptacle height.*—About 3 cm.

*Ray florets.*—Ray floret development has not observed.

*Disc florets.*—Shape: Fused in a tube. Apex: Acute. Length: About 1.4 cm. Diameter, apex: About 1.5 mm. Diameter, base: About 0.5 mm. Number of disc florets per inflorescence: About 15. Texture: Smooth, glabrous. Color, immature: Close to 186B. Color, mature: Mid-section and towards the apex, close to 186C; base, close to 182C to 182D.

*Phyllaries.*—Quantity per inflorescence: About 15 in about five whorls. Length: About 3 mm. Width: About 1.5 mm. Shape: Narrowly elliptic to narrowly ovate. Apex: Acute. Base: Cuneate. Margin: Entire. Texture, upper and lower surfaces: Smooth, glabrous. Color, upper surface: Close to 186A to 186B. Color, lower surface: Close to 186D to lighter than 186D.

*Peduncles.*—Length: About 7.1 cm to 15.2 cm. Diameter: About 2 mm. Strength: Strong. Aspect: Upright to 15° from vertical. Texture: Smooth, glabrous. Color: Close to N186C.

*Reproductive organs.*—Androecium: Quantity per floret: About five. Anther shape: Lanceolate. Anther length: About 1.5 mm. Anther color: Close to 187A. Pollen amount: Scarce. Pollen color: Close to 13A. Gynoecium: Quantity per floret: One. Pistil length: About 1.2 cm. Stigma color: Close to 75B to 75C. Style length: About 7 mm. Style color: Close to 69D. Ovary color: Close to 145A. Seeds/fruits: Seed and fruit development have not been observed.

Disease/pest resistance: Plants of the new *Eupatorium* have not been shown to be resistant to pathogens and pests common to *Eupatorium.*

Garden performance: Plants of the new *Eupatorium* have exhibited good tolerance to rain and wind and have been observed to be suitable for USDA Zone 6.

It is claimed:

1. A new and distinct *Eupatorium* plant named 'Baby Joe' as illustrated and described.

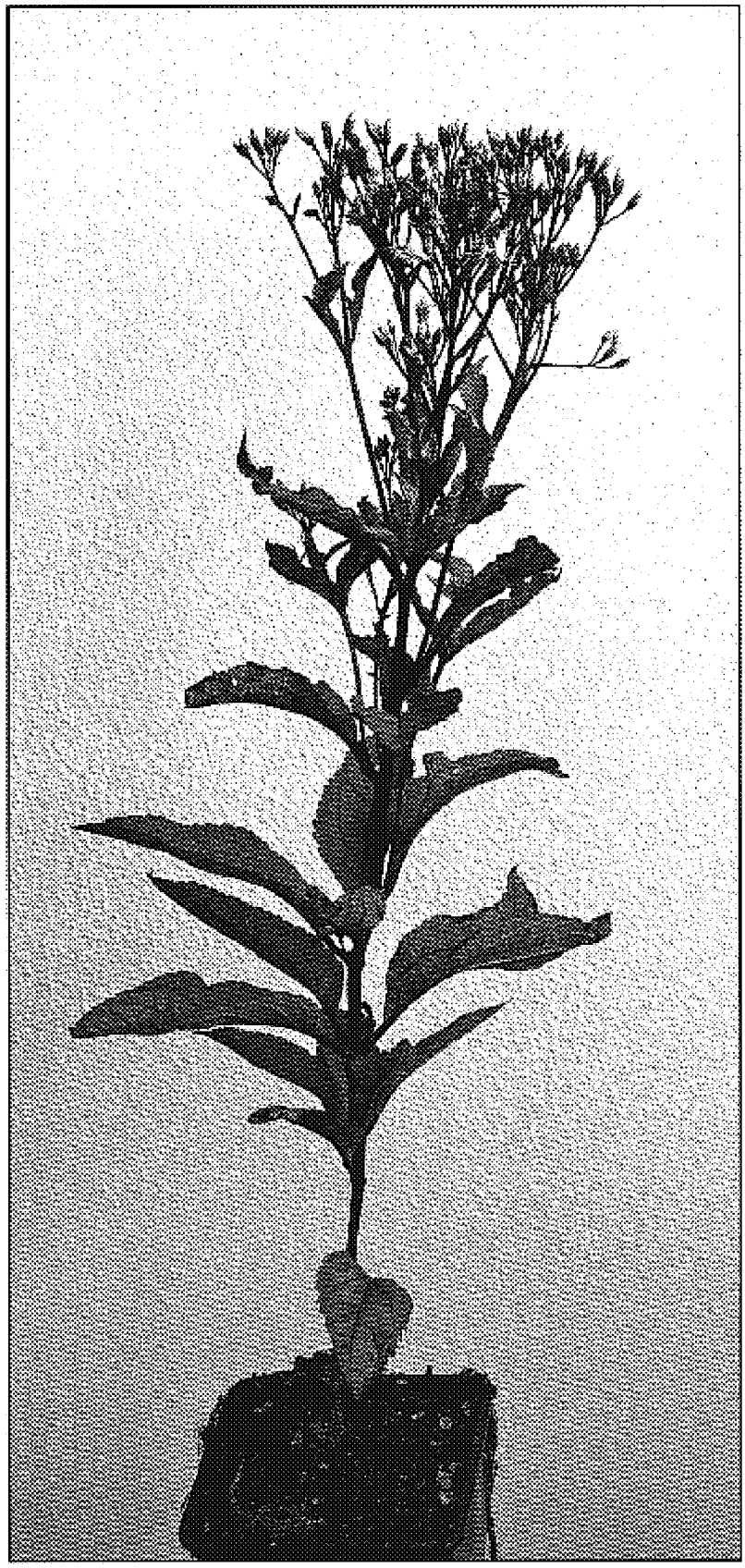

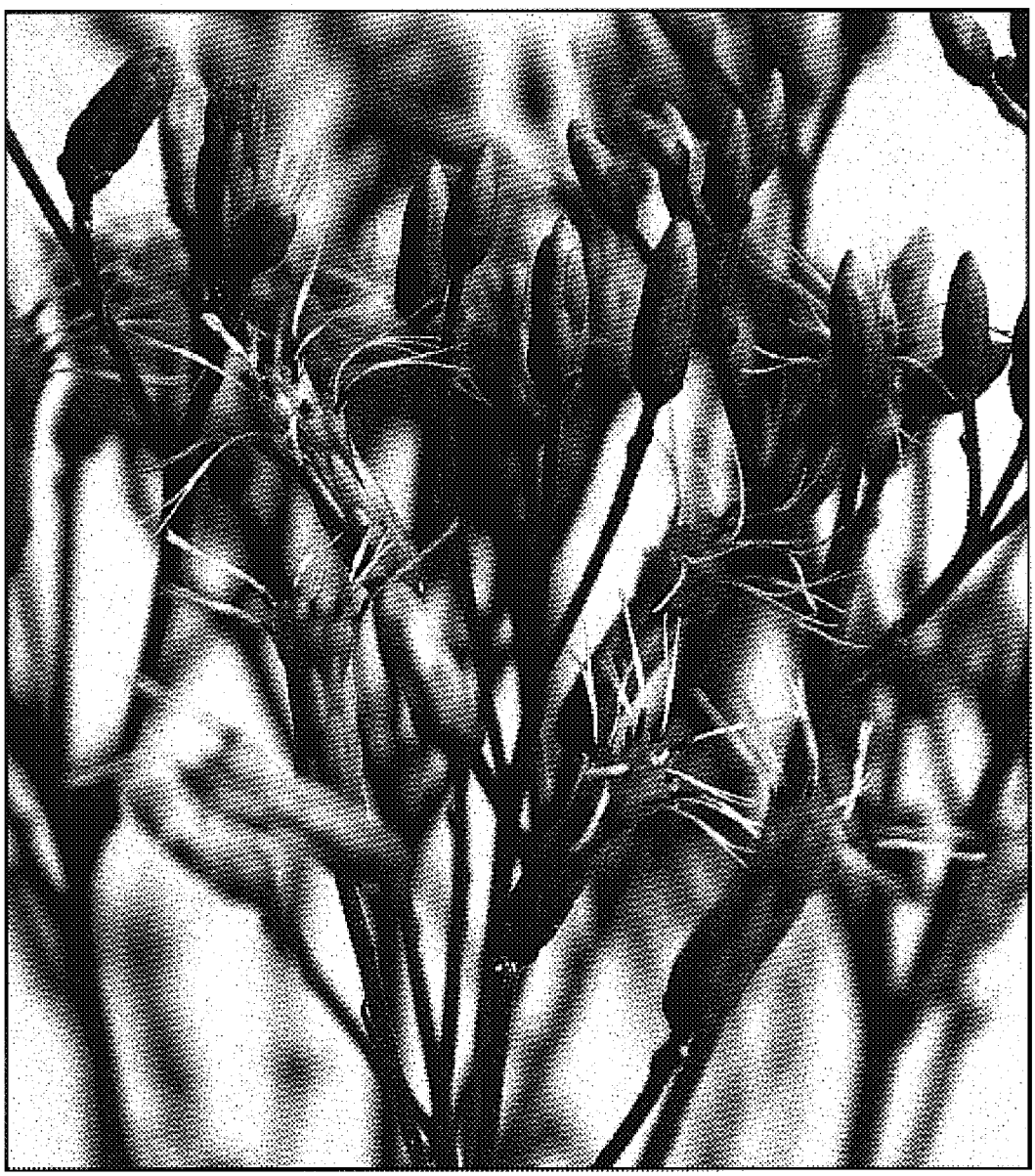
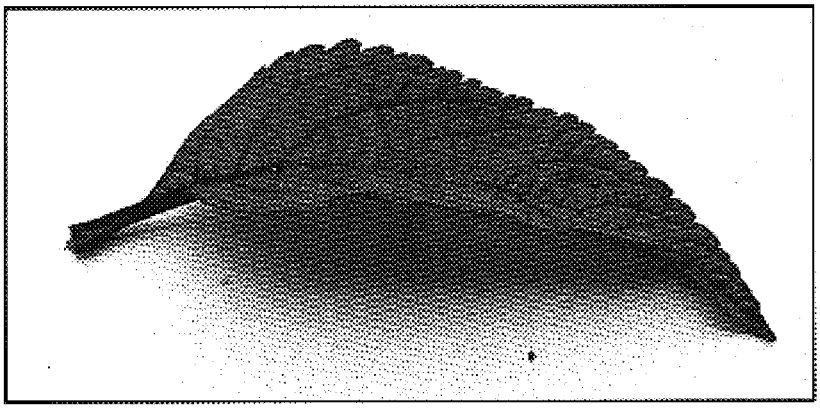

* * * * *